United States Patent [19]
Grimsby

[11] Patent Number: 4,640,754
[45] Date of Patent: Feb. 3, 1987

[54] PROCESS FOR THE PRODUCTION OF DICHLOROHYDRIN
[75] Inventor: F. Norman Grimsby, Houston, Tex.
[73] Assignee: Shell Oil Company, Houston, Tex.
[21] Appl. No.: 814,346
[22] Filed: Dec. 27, 1985
[51] Int. Cl.$^4$ .................. C25B 3/06; B01D 13/02
[52] U.S. Cl. .................. 204/182.4; 204/81; 204/302
[58] Field of Search .............. 204/182.4, 182.3, 72, 204/81

[56]  References Cited
U.S. PATENT DOCUMENTS
3,359,194 12/1967 Kollsman .................. 204/182.3

Primary Examiner—Howard S. Williams
Attorney, Agent, or Firm—Ronald R. Reper

[57] ABSTRACT

A continuous process for the production of dichlorohydrin by the reaction of allyl chloride, water and chlorine in a reaction zone comprising a first reaction stage, a final reaction stage and optionally at least one intermediate reaction stage, where the reaction mixture from at least one reaction stage is electrodialyzed in at least one electrodialysis zone to remove ions formed during the reaction, whereas at least a portion of the reaction product from said final reaction stage is passed to the concentrate inlet of said at least one electrodialysis zone, and withdrawing an ion-containing reaction product concentrate stream from said electrodialysis zone, whereby any dichlorohydrin which passes into the concentrate stream in said at least one electrodialysis zone may be recovered.

8 Claims, 2 Drawing Figures

PROCESS FOR THE PRODUCTION OF DICHLOROHYDRIN

BACKGROUND OF THE INVENTION

This invention relates to an improved process for reacting allyl chloride, water and chlorine to produce dichlorohydrin. "Dichlorohydrin" is a term employed herein to designate the isomers 1,2-dichloro-3-hydroxypropane and 1,3-dichloro-2-hydroxypropane.

It is known to prepare an aqueous solution of dichlorohydrin by reacting in a reaction zone allyl chloride, water and chlorine in dilute aqueous phase.

U.S. Pat. No. 2,714,121, incorporated herein by reference, discloses producing halohydrins by using high dilution of e.g., 250 to 400 volume of water per volume of e.g., a halosubstituted hydrocarbon in aqueous medium with subsequent addition of the halogen, and keeping the organic by-product phase dispersed as fine particles.

U.S. Pat. No. 2,714,123, incorporated herein by reference, discloses producing an aqueous solution of dichlorohydrin in a series of reaction stages wherein substantially all of the water is fed to the first of the reaction stage and the other reactants added in substantially equimolar proportions into each of the reaction stages.

U.S. Pat. No. 3,909,382 discloses recovering acid values, such as hydrochloric acid formed during olefin chlorohydrination, by series flow through a plurality of electrodialysis stages to upgrade the acid to higher concentration.

From Japanese Patent No. 74,00369 it is known that the product mixture from the reaction of a lower olefin, chlorine and water can be electrodialyzed to remove the by-product ions of hydrogen and chlorine, and the ion-depleted chlorohydrin solution circulated to the single reaction zone, enabling the production of a concentrated aqueous chlorohydrin solution.

As disclosed in copending Application Ser. No. 814,331, filed Dec. 27, 1985, in a multistage reaction system increased selectivity to the desired dichlorohydrin may be obtained by electrodialyzing the reaction effluent of one stage prior to being fed to a subsequent stage. Such electrodialyzing is advantageously carried out by neutralizing the removed acid in the concentrate stream of the electrodialysis zone as disclosed in copending Application Ser. No. 814,333, filed Dec. 27, 1985. A disadvantage of such procedures is that the electrodialysis membranes are somewhat permeable to the desired dichlorohydrin product and other haloorganics resulting not only in yield loss to the concentrate stream or streams, but also that the presence of such haloorganics in the aqueous concentrate stream requires energy intensive treatment to reduce the amount of organics to levels acceptable in receiving bodies of water such as rivers, lakes and the like. A further problem is that in the electrodialysis of hydrochloric acid, current efficiency becomes lower with increasing differences in hydrochloric acid concentration between the concentrate, i.e., ion receiving stream and the diluate i.e., ion depleting stream. The present invention provides a solution to these difficulties.

SUMMARY OF THE INVENTION

According to the invention, there is provided in a continuous process for the production of dichlorohydrin by the reaction of allyl chloride, water and chlorine in a reaction zone comprising a first reaction stage, a final reaction stage, and optionally at least one intermediate reaction stage, where the reaction mixture from each reaction stage, before entering the next reaction stage is electrodialyzed in a separate electrodialysis zone to remove ions formed during said reaction, the improvement which comprises passing at least a portion of the reaction product from said final reaction stage to the concentrate inlet of each said electrodialysis zone, and withdrawing an ion-containing reaction product from such said electrodialysis zone, whereby any dichlorohydrin which passes into the concentrate stream in said each electrodialysis zone may be recovered.

THE DRAWINGS

DESCRIPTION OF PREFERRED EMBODIMENTS

Figure 1:
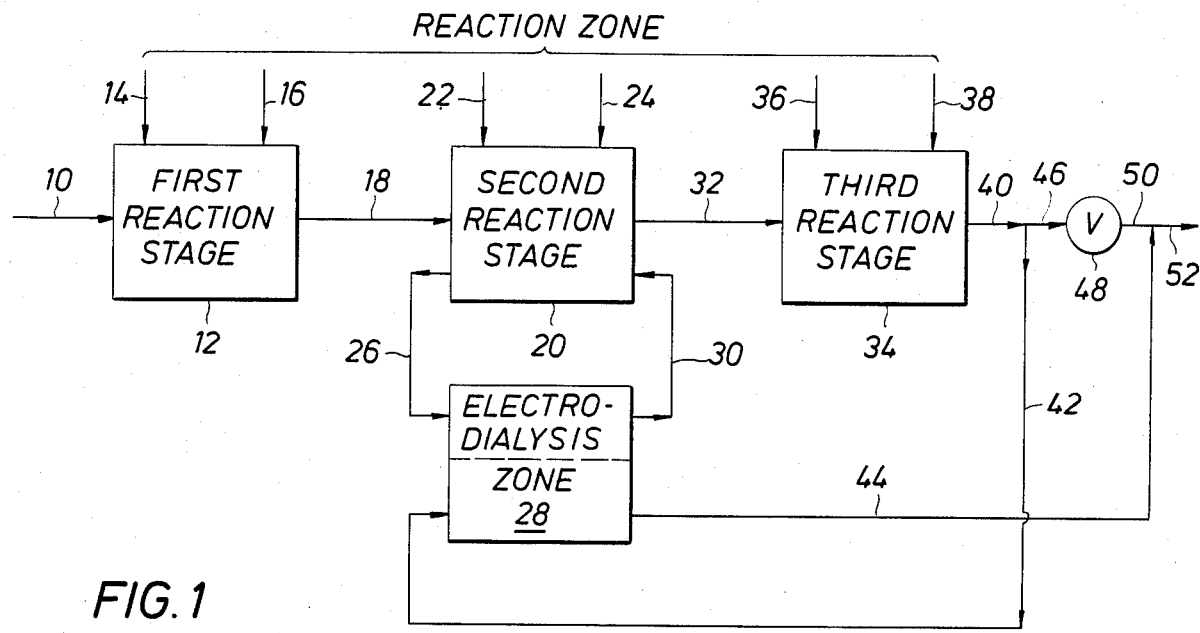
FIG. 1 depicts a schematic flow diagram of a preferred embodiment of the invention.

In the principal reaction, allyl chloride is converted to a mixture of the two isomers of glycerol dichlorohydrin by reaction with hypochlorous acid, HClO, which is readily formed when chlorine is dissolved in water. The dichlorohydrination reaction takes place readily at temperatures in the range from about 15° to about 55° C. Decreased temperature rapidly increases the amount of dissolved chlorine as well as the concentration of the hypochlorous acid. For maximum chlorohydrin yield it is necessary to run the reaction at low concentrations of chloride ion and of chlorohydrin, i.e., with high water dilution which reduces the formation of undesired by-products e.g., trichloropropane and tetrachloropropyl ether.

The reaction zone effluent typically has a low pH, resulting from the hydrogen chloride formed as by-product in the formation of the dichlorohydrin.

As disclosed in copending application Ser. No. 814,333, filed Dec. 27, 1985, that conditions within each reaction stage may be continually maintained to obtain higher pH selectivity by continual removal of the by-product hydrochloric acid, which removal by electrodialysis is rendered more efficient by neutralization of said acid after separation from the feed into the concentrate stream. The addition of a basic material to the concentrate stream for such neutralization substantially avoids back diffusion of the removed hydrogen ions into the dilute stream(s) and results in more efficient (more ion removal per unit of electrical power applied) electrodialysis of the reaction stage medium.

The present invention, which may be used alone or in combination with the concentrate neutralization procedure of said Ser. No. 814,333, concerns diverting at least a portion of the final stage effluent to the inlet concentrate stream of at least one electrodialysis zone used in combination with the multistage reaction zone, and then combining the ion enriched outlet electrodialysis concentrate stream with any undiverted portion of the final reaction stage effluent for further processing. In a preferred embodiment, the combined concentrate and reaction stage effluent, or where the total final reaction stage effluent is diverted to the concentrate inlet stream(s) of the electrodialysis zone(s), then the entire concentrate stream may be subjected to further processing. Such further processing preferably involves conversion of the dichlorohydrin to epichlorohydrin by reacting with an excess of a basic acting agent and flash distillation of the resulting epichlorohydrin at atmospheric pressure or superatmospheric pressure as disclosed e.g., in Engs et al, U.S. Pat. No. 2,177,419.

Electrodialysis is by now a well established industrial process. Basically, an electrodialysis unit comprises a plurality of membranes alternately anionic and cationic placed between an anode and a cathode connected to a direct current source. The membranes are usually separated from each other by 1 to 5 mm using appropriate spacers and the feed stream may be made to flow through a spacer creating a turbulent path in order to increase turbulence of the liquids contacting the membranes or insheet-type flow to reduce pumping pressure. The construction of the unit is generally in the form of a stack, like a filter stack. The membranes which usually contain ion exchange groups have a fixed positive or negative charge. The cationic membranes have negative fixed charges; the anionic membranes have positive fixed charges. Electrical neutrality in the membrane matrix is satisfied by the migrating cations (through cationic membranes) and anions, (through anionic exhange membranes).

If a feed stream is introduced uniformly from the top of the electrodialysis unit, it would be found that passages in the unit having an anion membrane of the cathode side of the passage and vice versa will become concentrate streams higher in ionized (herein saline) components and the other streams in passages bounded by anion membranes on the anode side and cathode membranes on the cathode side will become depleted in ionized components. Such depleted stream or streams are herein referred to as the diluate stream.

When a direct current is applied across the two electrodes (anode and cathode) anions will tend to migrate towards the anode passing through the anion exchange membrane and being stopped by the first cation exchange membrane. In like manner, cations will cross through the cationic exchange membrane and will be stopped by the anionic exchange membranes. However, non-electrolyte species are not prevented from passing through the exchange membranes, except in so far as these are made of a tighter pore structure, even so, however, non-electrolytes will migrate through the membranes, the actual amount of migration depending on relative volume of dilate/concentrate streams.

The anionic and cationic membranes employed herein are known in the art. Generally, the anionic and cationic membranes comprise flat sheets of inorganic or organic materials which have extreme water-insolubility. Preferably the anionic and cationic membranes are prepared from synthetic organic resinous, polymeric materials, (e.g., polystrene polymers) to which are bonded ionic groups. Any strong or weak base (e.g., tertiary amines or quaternary ammonium compounds) can be chemically bonded to the organic material to form cationic membranes; any strong or weak acid (e.g., aryl sulfonates) can be chemically bonded to the organic resinous material to form anionic membranes.

Generally, the anionic and cationic membranes herein, either in the form of laminate or a homogeneous cast or sheet, are "backed" or reinforcing fabric, for example, fiberglass or Dynel (Dynel is a trade name for modified acrylic polymers), to provide them with a substantially rigid structure. Other 'backings' can be used, provided the anionic and cationic membranes remain essentially impervious to mass flow but porous enough to permit ion migration or transfer. cationic membranes remain essentially impervious to mass flow but porous enough to permit ion migration or transfer.

The cation and anion-exchange membranes can be any cation- and anion-selective membranes respectively which are essentially stable in the feed water and not chemically degraded by the components therein. Exemplary membranes are disclosed in the article entitled "Electrodialysis", Kirk-Othmer, Encyclopedia of Science and Technology, pages 846–865 (Second Edition, Interscience Publishers, 1965) and U.S. Pat. Nos. 2,730,768, 2,762,272, 2,860,097 and 3,616,385 incorporated herein by reference.

Generally, for stability of the membranes, it is necessary to employ temperatures below about 70° C. during electrodialysis. In terms of overall efficiency, it is preferred to carry out the electrodialysis step at about the temperature within the reaction stage served by each electrodialysis unit e.g., from about 15° to about 50° C. with temperatures from about 40° to 50° C. being preferred.

Figure 2:
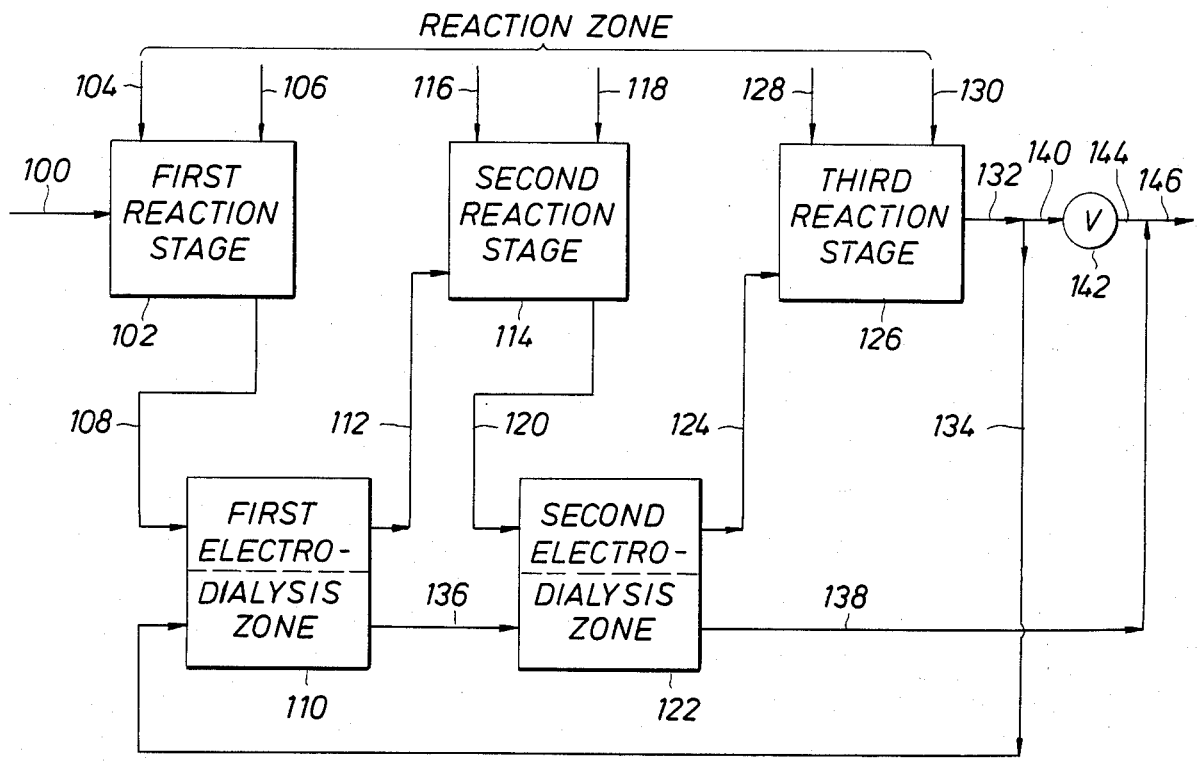
FIG. 2 depicts a schematic flow diagram of another preferred embodiment of the invention.

An embodiment of the invention will be described with reference to FIG. 1 which shows diagrammatically a preferred assemblage according to the invention wherein the single electrodialysis zone is employed in parallel flow with the second reaction stage of a three stage reaction zone. In FIG. 1 a fresh water stream is continuously introduced through conduit 10 into a first reaction stage 12. The reaction stage may comprise a stirred or agitated vessel but preferably is a circulating loop reactor as shown and described in greater particularity in U.S. Pat. No. 2,714,121. Preferably the first stage and each subsequent stage is sized to permit circulation of the reaction components at a rate of at least 250 up to about 400 times the volume of allyl chloride added to reach reaction stage. Allyl chloride is introduced into said first reaction stage 12 via line 14 and chlorine is added in substantially equimolar amount via line 16. A portion of the first stage reaction mixture containing about 0.2M dichlorohydrin and 0.2N HCl is continuously passed via line 18 to the second reaction stage 20, where additional allyl chloride is added via line 22 and additional water is added via line 24. A portion of the reaction mixture from the second stage is continuously passed via line 26 to an electrodialysis zone 28. The amount of reaction mixture passed to the electrodialysis zone 28 may vary considerably, depending upon the reaction temperature, membrane area and particular electrodialysis conditions, e.g. the particular membranes, applied voltage etc., but will generally be in the volume ratio range from about 0.5 to 20, normally 1 to 10 and particularly from about 2 to 6 volumes per volume of throughput per reaction stage. A portion of the second stage reaction mixture having a temperature in the range from about 40° to 55° C. is fed to electrodialysis zone 28 comprised of alternating anionic exchange membranes designated as 203QZL-386 and cationic exchange membranes designated as 61 CZL-386 which membranes are available from Ionics, Inc., Watertown, Mass. In general the voltage across each stack of membranes is arranged so that there is a voltage of about 0.5 to about 3.0 volts per cell pair, with a voltage in the range from about 1.0 to 2.5 being preferred. The ions are removed into a concentrate stream which enters the electrodialysis zone via line 42, and exits via line 44. From electrodialysis zone 28 a diluate stream comprising about 0.4M dichlorohydrin and about 0.01N HCl is returned via line 30 to the second reaction stage 20. The reaction effluent from the second stage is continuously passed via line 32 to a third reaction stage 34, to which additional allyl chloride is added via line 36 and additional chlorine via line 38. The reaction product from the third stage 34 is passed via line 40 and a portion is passed via line 42 as the concentrate inlet to electrodialysis zone 28. The ion receiving concentrate zone is passed from said electrodialysis zone via line 44 and is recombined with any third stage reaction effluent passing from said stage via line 46, valve 48 lines 50 and 52. As may be seen valve 48 provides control to divert a small or large amount of the third stage reaction effluent to the electrodialysis zone as may be desired. Ordinarily this will amount to at least about 25% of the reaction stage effluent in order to assure a low concentration gradient of the ion between the feed and concentrate feeds to the electrodialysis zone. Although FIG. 1 depicts a single electrodialysis zone, the flow scheme according to the invention may be applied to like schemes where an electrodialysis zone is provided for all or nearly all reaction stages. In such event the last stage reaction effluent may be supplied to the concentrate inlet of each electrodialysis zone individually as shown in FIG. 1, or in series flow as shown in FIG. 2. In the event of series flow to a plurality of electrodialysis zones it is preferred to divert a large portion, e.g., 50 or 75% or even 100% of the third stage reaction effluent through the electrodialysis zones in order to maintain as low a concentration gradients between the inlet feed and concentrate inlet to electrodialysis zones which enables higher electrodialysis efficiency.

The embodiment of FIG. 2 illustrates the invention applied to interstage electrodialysis of the reaction effluent from a three stage reaction zone. This invention may be readily applied to a reaction zone comprising three, four, five, six or more reaction stages, with electrodialysis in parallel flow to one or more reaction stages as shown in FIG. 1 or in series flow between reaction stages as shown in FIG. 2.

In FIG. 2 water is introduced via line 100 into the first reaction stage 102. Allyl chloride is added via line 104 and chlorine via line 106. The first stage reaction effluent is continuously passed via line 108 to first electrodialysis zone 110 comprised and operated substantially as described for electrodialysis zone 28 in FIG. 1. Ions from the first reaction stage feed electro migrate into the concentrate stream provided to said first electrodialysis zone 110 via line 134, which ion-enriched stream exits said zone via line 136. From said first stage elextrodialysis zone 110, a diluate stream having lowered ion content is passed via conduit 112 to a second reaction stage 114, wherein additional allyl chloride is continuously fed via line 116 and a substantially equimolar amount of chlorine via line 118. Reaction effluent from said second stage is passed via line 120 to second electrodialysis zone 122 comprised and operated substantially like first electrodialysis zone 110. In the second electrodialysis zone 122, ions are electromigrated from the second stage effluent into a concentrate stream provided by line 136, which ion-enriched stream exits the second electrodialysis zone 122 via line 138. The diluate stream having lowered ion content is passed via line 124 to third reaction stage 126, wherein as with previous reaction stages, allyl chloride and chlorine are added in substantially equimolar amounts via conduits 128 and 130, respectively. The third stage reaction mixture is pased via lines 132, 140, valve 142 and lines 144 and 146 for conversion to derivatives such as epichlorohydrin and/or glycerine. A portion of the third stage reaction effluent is diverted via line 134 to first electrodialysis zone 110, thence via line 136 to second electrodialysis zone 122 and having been further enriched by the small amount of dichlorohydrin which passes through the membranes of each electrodialysis unit, is then recombined with the third reaction stage effluent. In this manner the overall yield advantages by the use of electrodialysis of the reaction stage is further enhanced, and the costs associated with treatment of the organics-containing concentrate stream prior to disposal are substantially avoided. The flow stream of the present invention may advantageously be employed in combination with the addition of a basic material to the concentrate stream (not shown) as described in copending application Ser. No. 814,333 filed Dec. 27, 1985.

What is claimed is:

1. In a continuous process for the production of dichlorohydrin by the reaction of allyl chloride, water and chlorine in a reaction zone comprising a first reaction stage, a final reaction stage, and at least one intermediate reaction stage, where the reaction mixture from at least one reaction stage, before entering the next reaction stage is electrodialyzed in a separate electrodialysis zone having a feed inlet and a concentrate inlet, to remove ions formed during said reaction, the improvement which comprises passing at least a portion of the reaction product from said final reaction stage to the concentrate inlet of said at least one electrodialysis zone, and withdrawing an ion-containing reaction product concentrate stream from such said electrodialysis zone, whereby any dichlorohydrin which passes into the concentrate stream in said at least one electrodialysis zone may be recovered.

2. A process as in claim 1 wherein the reaction zone comprises from 3 to 6 reaction stages.

3. A process as in claim 1 wherein said at least one electrodialysis zone is arranged to electrodialyze the reaction mixture in series flow between two reaction stages.

4. A process as in claim 1 wherein said at least one electrodialysis zone is arranged to electrodialyze the reaction mixture from a reaction stage in parallel flow with said reaction stage.

5. A process as in claim 1 wherein at least 50%V of the reaction mixture effluent from the final reaction stage is diverted to the concentrate inlet streams of at least one said electrodialysis zone.

6. A process as in claim 1 wherein at least 75%V of the reaction mixture effluent from the final reaction stage is diverted, directly or indirectly, to the inlet concentrate stream of the electrodialysis zone which electrodialyzes the reaction mixture from the final reaction stage.

7. A process as in claim 1 wherein the final stage reaction mixture effluent is diverted, directly or indirectly to the inlet concentrate stream of the electrodialysis zone which electrodialyzes the reaction mixture from the final reaction stage.

8. A process as in claim 1 wherein at least 25%V of the final stage product reaction mixture is diverted to the inlet concentrate stream of a first electrodialysis zone which electrodialyzes the reaction mixture from the first reaction stage and then to the inlet concentrate stream of at least one subsequent electrodialysis zone.

* * * * *